(12) United States Patent
Ohishi et al.

(10) Patent No.: US 6,187,977 B1
(45) Date of Patent: Feb. 13, 2001

(54) PROCESS FOR PRODUCING CHLORINATED TERTIARY CARBON-CONTAINING HYDROCARBONS

(75) Inventors: Takahiro Ohishi, Kobe; Takeshi Kawamura, Akashi; Akihisa Hirota, Kakogawa; Takuya Maeda, Ibaraki; Hiroshi Tsuneishi, Kobe; Shun Wachi, Takasago, all of (JP)

(73) Assignee: Kaneka Corporation, Osaka (JP)

( * ) Notice: Under 35 U.S.C. 154(b), the term of this patent shall be extended for 0 days.

(21) Appl. No.: 09/300,406

(22) Filed: Apr. 27, 1999

(30) Foreign Application Priority Data

Apr. 27, 1998 (JP) .................................................. 10-116493
Jun. 9, 1998 (JP) .................................................. 10-160044

(51) Int. Cl.$^7$ .................................................. C07C 17/00
(52) U.S. Cl. .......................................... 570/196; 570/261
(58) Field of Search ...................................... 570/196, 261

(56) References Cited

FOREIGN PATENT DOCUMENTS 9-143106    6/1997   (JP) .

Primary Examiner—Alan Siegel

(74) Attorney, Agent, or Firm—Pollock, Vande Sande & Amernick

(57) ABSTRACT

The present invention thus provides a process for producing (D) a chlorinated hydrocarbon compound of the general formula (2):

$$C_n R^1{}_m H_k (CR^2 R^3 Cl)_j \qquad (2)$$

[wherein n is an integer of 1 to 12, m and k each independently is an integer of 0 to 25, j is an integer of 1 to 10; $R^1$ represents an atom selected from the group consisting of chlorine, bromine, iodine, oxygen, nitrogen, sulfur and phosphorus and, when m is 2 or more, the two or more $R^1$ groups may be the same or different, the group $C_n R^1{}_m H_k$ having a valence of j does not contain any tertiary carbon-hydrogen bond; and $R^2$ and $R^3$ each independently represents a saturated aliphatic hydrocarbon group containing 1 to 5 carbon atoms or a group derived therefrom by substitution of a halogen atom or atoms for some hydrogen atom or atoms thereof and not containing a tertiary carbon-hydrogen bond], which process comprises adding (C) a protic acid to a mixture of
(A) a compound of the general formula:

$$C_n R^1{}_m H_k (CHR^2 R^3)_j \qquad (1)$$

[wherein m, n, k, j, $R^1$, $R^2$ and $R^3$ are as defined above] and (B) an aqueous solution of a metal hypochlorite.

19 Claims, No Drawings

PROCESS FOR PRODUCING CHLORINATED TERTIARY CARBON-CONTAINING HYDROCARBONS

FIELD OF THE INVENTION

The present invention relates to a process for producing a chlorinated hydrocarbon compound. More particularly, it relates to a process for selectively chlorinating a tertiary carbon atom(s) of a hydrocarbon compound by using a hypochlorous acid compound.

The thus-synthesized compounds having a chlorinated tertiary carbon atom are useful as a reagent in various syntheses which utilize the reactivity of a chlorine substituent. For example, an aromatic group-substituted chlorinated hydrocarbon such as 1,4-bis(1-chloro-1-methylethyl)benzene (1,4-dicumyl chloride, p-Cl(CH$_3$)$_2$CC$_6$H$_4$C(CH$_3$)$_2$Cl) is known to be useful as a cationic polymerization initiator in the production of terminally functional polyisobutylene and the like [U.S. Pat. Nos. 4,276,394 and 5,527,870 (Maeda et al., 1994)].

PRIOR ART

As a process for producing such a initiator, the following processes are known which use 1,4-diisopropylbenzene as a starting material.

One comprises synthesizing 1,4-diisopropenylbenzene (CH$_2$=(CH$_3$)CC$_6$H$_4$C(CH$_3$)=CH$_2$) by dehydrogenation (U.S. Pat. No. 3,429,941) and subjecting the same to hydrogen chloride addition reaction (O. Nuyken et al., Makromol. Chem., 186, 173 (1985)). Another known process comprises synthesizing 1,4-bis(1-hydroxy-1-methylethyl)benzene (1,4-HO(CH$_3$)$_2$CC$_6$H$_4$C(CH$_3$)$_2$OH) by oxidation with air (e.g. Japanese Kokai Publication Sho-60-174737) and reacting the same with hydrogen chloride (V. S. C. Chang et al., Polymer Bulletin, 4, 513 (1981)).

While at least two reaction procedures are required in the syntheses mentioned above, a one-step process reported for synthesizing the desired 1,4-dicumyl chloride comprises reacting 1,4-diisopropylbenzene (1,4-H(CH$_3$)$_2$CC$_6$H$_4$C(CH$_3$)$_2$H) with chlorine gas under sunlight irradiation (M. S. Kharashch et al., J. Am. Chem. Soc., 61, 2142 (1939)). In the reaction under sunlight irradiation, however, to control the selectivity concerning the chlorine substitution sites is a problem.

On the other hand, a process reported for obtaining 1,4-dicumyl chloride by chlorinating 1,4-diisopropylbenzene at the benzyl sites thereof comprises reacting with sodium hypochlorite in the presence of a phase transfer catalyst (Bu$_4$N(HSO$_4$)) (H. E. Fonouni et al., J. Am. Chem. Soc., 1983, 105, 7672). However, this process uses an expensive phase transfer catalyst, hence cannot be said to be an industrially advantageous process. A process which comprises effecting chlorination with hypochlorous acid without using any phase transfer catalyst has also been reported (F. Minisci et al., Chim. Ind., 70, 52 (1988); Japanese Kokai Publication Hei-09-143106).

The process for obtaining 1,4-dicumyl chloride by chlorinating a tertiary carbon of 1,4-diisopropylbenzene by use of hypochlorous acid involves only one reaction step and is effective and higher in selectivity as compared with photo-chlorination. However, hypochlorous acid is a very unstable substance and it is difficult to prepare and store hypochlorous acid always at a constant concentration. Therefore, even when constant charge amounts are set for the raw materials, it is difficult to attain a stable reaction yield, selectivity and product quality due to fluctuation of the equivalent relationship.

Furthermore, when hypochlorous acid is employed, it is necessary to neutralize the hypochlorous acid with an alkali for terminating the reaction. On the other hand, the product 1,4-dicumyl chloride is very unstable against water in an alkaline medium and, when it is in contact with water, the hydrolysis reaction will proceeds, leading to quality deterioration.

1,4-Dicumyl chloride is also deteriorated when in contact with a metal. Means conceivable for overcoming this disadvantage is to employ glass lining or Teflon lining in most of the process equipment. With such material, however, electrostatic elimination by earthing is essentially difficult and therefore, when the liquid contents are electrically charged, there arises a risk of pinhole formation due to electrostatic sparking. Therefore, in the lined equipment, it is important to take adequate measures against static electricity. A known measure against static electricity comprises adding an antistatic agent. In some instances, however, this method is unfavorable since the antistatic agent, if remaining in the product, may affect the quality thereof.

While the production of 1,4-dicumyl chloride by using hypochlorous acid is disclosed in Japanese Kokai Publication Hei-09-143106 as well, the technology of Japanese Kokai Publication Hei-09-143106 cannot be said to be a production process suited for industrial application, since the problem mentioned above has not been solved.

The problem to be solved in conducting the chlorination reaction by using a hypochlorous acid compound effectively is how to introduce chlorine selectively into desired sites alone. Hypochlorous acid, which is required for said reaction, is a very unstable substance and it is difficult to prepare and store hypochlorous acid always at a constant concentration. In the conventional procedure for preparing hypochlorous acid by admixing hydrogen chloride, chlorine gas is produced, hence it cannot be said to be an industrially advantageous procedure from the safety viewpoint and for the reason that the utilization percentage of the raw material sodium hypochlorite is reduced. The thus-prepared hypochlorous acid tends to decrease in its concentration until it is used in the chlorination reaction. Therefore, it becomes impossible to charge hypochlorous acid in a constant amount relative to the reactant to be chlorinated and, as a result, it is difficult to obtain a stable reaction yield, selectivity, and a product quality.

Another essential point in improving the reaction selectivity and yield and realizing quality stabilization is how to terminate the chlorination reaction. A known method of deactivating hypochlorous acid to terminate the reaction comprises making the medium alkaline and then adding sodium sulfite. However, investigations made by the present inventors revealed that the obtained chlorination product is subject to hydrolysis when in contact with water in an alkaline medium. Therefore, said method can hardly be employed as it is.

Furthermore, there is a major problem from the industrial application viewpoint, namely measures against static electricity in cases where lined equipment is used. In the process according to the present invention, the chlorination product obtained, if in contact with a metal, will be deteriorated. Since a protic acid is used, the equipment, if made of an ordinary metal, will be corroded. Corrosion-resistant metals are indeed available, such as tantalum, platinum and gold, but these are special materials and are very expensive, hence the use thereof is not practical. For these reasons, it is thought that lined equipment should be used in industrial application of the process. In such equipment, however, there is a risk of pinhole formation due to sparking if measures against static electricity are not taken. Sparking becomes particularly significant when the content liquid tends to be easily charged electrostatically. The content liquid occurring as a slurry as a result of crystallization is known to be especially readily chargeable and therefore measures against static electricity are very important in the step of crystallization. As a measure against static electricity, there is a method comprising adding an antistatic agent. However, the antistatic agent, if remaining in the product, may unfavorably affect the quality of the product.

SUMMARY OF THE INVENTION

It is an object of the present invention to solve the problems encountered in chlorinating the tertiary carbon atom or atoms of a hydrocarbon compound by using hypochlorous acid, namely the reaction selectivity and operability problems, the problems concerning the method of terminating the reaction, and the problems concerning the measures against static electricity for enabling industrial application of the process in question. As a result of intensive investigations made by the present inventors to explore in detail and solve these problems, it was found that the above problems can be solved by carrying out the reaction in the presence of hydrochloric acid added to the reactant mixture, adding hydrochloric acid added to the organic layer after termination of the reaction, and effecting crystallization after adding hydrochloric acid to the organic layer after completion of the reaction as a measure against static electricity. Such findings have now led to completion of the present invention.

The present invention thus provides a process for producing a chlorinated hydrocarbon compound (D) of the general formula (2):

$$C_nR^1{}_mH_k(CR^2R^3Cl)_j \qquad (2)$$

[wherein n is an integer of 1 to 12, m and k each independently is an integer of 0 to 25, j is an integer of 1 to 10; $R^1$ represents an atom selected from the group consisting of chlorine, bromine, iodine, oxygen, nitrogen, sulfur and phosphorus and, when m is 2 or more, the two or more $R^1$ groups may be the same or different, the group $C_nR^1{}_mH_k$ having a valence of j does not contain any tertiary carbon-hydrogen bond; and $R^2$ and $R^3$ each independently represents a saturated aliphatic hydrocarbon group containing 1 to 5 carbon atoms or a group derived therefrom by substitution of a halogen atom or atoms for some hydrogen atom or atoms thereof and not containing a tertiary carbon-hydrogen bond], which comprises adding (C) a protic acid to a mixture of (A) a compound of the general formula:

$$C_nR^1{}_mH_k(CHR^2R^3)_j \qquad (1)$$

[wherein m, n, k, j, $R^1$, $R^2$ and $R^3$ are as defined above] and
(B) an aqueous solution of a metal hypochlorite.

The present invention also provides a process for producing a chlorinated hydrocarbon compound which comprises synthesizing (D) a compound of the general formula (2) shown above by using
(A) a compound of the general formula (1) shown above,
(B) an aqueous solution of a metal hypochlorite and
(C) a protic acid,
and thereafter adding
(E) a protic acid to the organic layer.

The present invention further provides a process for producing a chlorinated hydrocarbon compound which comprises using (F) an organic solvent when synthesizing
(D) a compound of the general formula (2) shown above by using
(A) a compound of the general formula (1) shown above,
(B) an aqueous solution of a metal hypochlorite and
(C) a protic acid.

DETAILED DESCRIPTION OF THE INVENTION

The compound to be used as the starting material in the process of the present invention generally includes a compound of the general formula (1):

$$C_nR^1{}_mH_k(CHR^2R^3)_j \qquad (1)$$

[wherein n is an integer of 1 to 12, m and k each independently is an integer of 0 to 25, j is an integer of 1 to 10; $R^1$ represents an atom selected from the group consisting of chlorine, bromine, iodine, oxygen, nitrogen, sulfur and phosphorus and, when m is 2 or more, the two or more $R^1$ groups may be the same or different, the group $C_nR^1{}_mH_k$ having a valence of j does not contain any tertiary carbon-hydrogen bond; and $R^2$ and $R^3$ each independently represents a saturated aliphatic hydrocarbon group containing 1 to 5 carbon atoms or a group derived therefrom by substitution of a halogen atom or atoms for some hydrogen atom or atoms thereof and not containing a tertiary carbon-hydrogen bond]. $R^2$ and $R^3$ in the above formula each independently is, for example, a hydrocarbon group such as methyl, ethyl or n-propyl, or a substituted hydrocarbon group with at least one substituent, such as a chlorine atom, on a carbon atom thereof.

Among such compounds to be used as starting materials in the process of the present invention, those represented by the general formula (3):

$$C_6H_{6-z}(CHR^4R^5)_z \qquad (3)$$

[wherein z is an integer of 1 to 4 and $R^4$ and $R^5$ each independently is a saturated aliphatic hydrocarbon group containing 1 to 5 carbon atoms and having no tertiary carbon-hydrogen bond], are preferred. As examples of $R^4$ and $R^5$, there may be mentioned hydrocarbon groups such as methyl, ethyl and n-propyl.

As a preferred example of the compound of general formula (1) to be used in the process of the present invention, there may be mentioned the following one:

[Chemical 1]

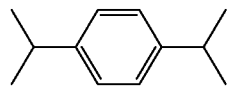

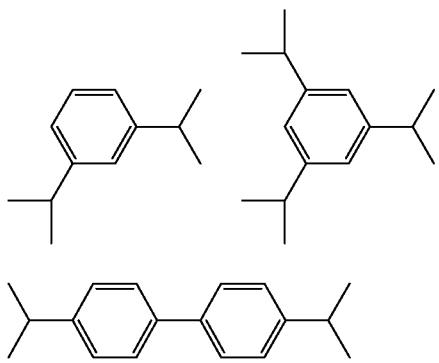

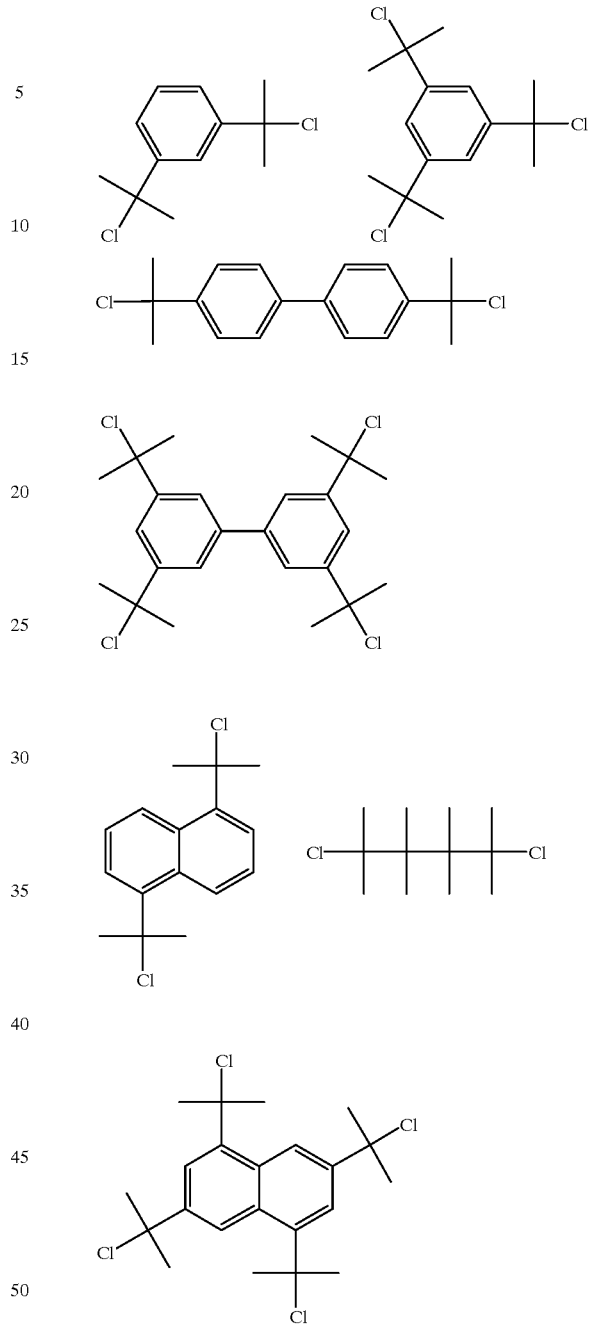

As a preferred example of the chlorinated hydrocarbon compound of general formula (2) obtainable by the process of the present invention, there may be mentioned the following one:

[Chemical 2]

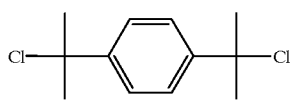

As the metal hypochlorite to be used in the process of the present invention, there may be mentioned, for example, potassium hypochlorite, sodium hypochloride, calcium hypochlorite, barium hypochlorite, cuprous hypochlorite and cupric hypochlorite. Among these, sodium hypochlorite is preferred because of ready commercial availability, ease of handling, and good reaction yield and selectivity.

The concentration of the aqueous solution of such metal hypochlorite is not critical but, generally, a concentration not lower than 0.7 mol/kg is preferred since the reaction yield and selectivity are good at such concentration. When the concentration of sodium hypochloride as made available is not lower than 0.7 mol/kg, the aqueous solution may be used after dilution with water. In that case, "water" means tap water, deionized water, distilled water or the like. In some instances, it may contain metal salts such as NaCl and KCl.

The amount of the aqueous metal hypochlorite solution to be used in the process of the present invention is not particularly restricted provided that the chlorine content is not lower than the stoichiometrically equivalent level. The use of an aqueous metal hypochlorite solution in large excess, however, may allow side reactions to proceed, resulting in a decreased purity of the desired product. Therefore, for obtaining the desired product with good efficiency and high purity, it is preferred that said solution be used in a molar amount 1.0 to 10 times, more preferably 1.0 to 5 times, the theoretical amount.

As examples of the protic acid to be used in the process of the present invention, there may be mentioned, for example, hydrochloric acid, sulfuric acid, nitric acid, acetic acid and dry ice. Among them, hydrochloric acid is preferred as the protic acid to be used in the reaction since it can afford a high reaction yield and selectivity. The protic acid is preferably added continuously or in several portions, although addition at once is also possible. In the case of continuous addition, the addition period is preferably 0.5 to 15 minutes, more preferably 1 to 5 minutes. The protic acid is used in an amount such that the pH of the aqueous layer in the reaction system is adjusted preferably to a value within the range of 2 to 9, more preferably 4 to 6. The concentration of the protic acid to be used is not particularly restricted but, from the viewpoints of quality, reaction time, and reactor capacity in industrial application, among others, it is preferred that said concentration be relatively high; hence concentrated hydrochloric acid having a concentration of not lower than 36% by weight is particularly preferred.

In cases where the hydrolyzate of the compound of general formula (2) as occurring in the organic layer after the reaction is to be converted to the compound of general formula (2) by contacting with hydrochloric acid, it is preferred that the concentration of hydrochloric acid to be contacted with the organic layer after reaction be not less than 3%, more preferably not less than 36% by weight. Since hydrochloric acid decomposes hypochlorous acid, the treatment for terminating the reaction and the treatment of the organic layer may be made simultaneously.

In the process of the present invention, while the reaction may be carried out without using any solvent, the reaction is preferably carried out in a solvent so that the starting material may be subjected to reaction in a diluted state. Preferred as the reaction solvent are, for example, toluene, benzene, ethylene dichloride, carbon tetrachloride, chloroform, methylene chloride, butyl chloride, propyl chloride and 1-trichloro-2-trifluoroethane. Chlorobenzene, trifluoromethylbenzene, ethyl chloride and benzene are particularly preferred among others.

Although the reaction temperature is not critical, it is preferred that the reaction be carried out at a low temperature, namely at −15° C. to 40° C., since hypochlorous acid is relatively unstable. At temperatures higher than 40° C. or lower than −15° C., the decomposition of hypochlorous acid is accelerated, so that the concentration thereof may decrease almost to zero in the middle of the reaction period. The decomposition of hypochlorous acid is accompanied by generation of dangerous chlorine gas. From the safety viewpoint as well, it is therefore preferred that the reaction be carried out at temperatures within the above range.

The alkali to be used for the treatment of the aqueous layer after completion of the reaction is not particularly restricted. Preferred, however, are metal hydroxides and metal alkoxides. More preferred are sodium hydroxide and potassium hydroxide for the reasons of ease of handling and ready availability. Sodium hydroxide or potassium hydroxide may be used in the form of a solid as it is or in the form of an aqueous solution. Sodium sulfite used for the treatment of the aqueous layer after pH adjustment may be used in the form of a solid or an aqueous solution. For the reasons of ease of handling and simplicity of procedure, it is preferably used in the form of an aqueous solution having a concentration of about 10%.

In the process of the present invention, when the obtained product occurs as a solid, it is preferred that the product be purified by crystallization. As the solvent to be used on that occasion, there may be mentioned, for example, hydrocarbons such as pentane, hexane, heptane, octane, cyclohexane, methylcyclohexane, ethylcyclohexane and toluene, and halogenated hydrocarbons such as carbon tetrachloride, chloroform, methylene chloride, chloroethane, dichloroethane, propyl chloride and butyl chloride. For obtaining the product with a high yield and high purity, the use of hexane, among others, as the solvent is preferred. For increasing the efficiency of crystallization, the amount of the solvent to be used in the step of crystallization is preferably set at an amount such that the weight of the solvent amounts to not more than 20 times that of the reaction mixture.

As mentioned hereinabove, the chlorination product obtained in the process of the present invention is deteriorated in quality when it is in contact with a metal. Therefore, using a lined vessel may be thought of. When crystallization is carried out using hexane as the solvent, the risk of pinhole formation due to electrostatic sparking is high, hence it is desirable that measures be taken against static electricity.

The concentration of hydrochloric acid to be used as a measure against static electricity in carrying out crystallization in a lined vessel is not particularly restricted but is preferably not higher than pH 5. The addition amount is not less than $1/10^8$, preferably not less than $1/100$, by volume relative to the reaction mixture.

PREFERRED EMBODIMENTS OF THE INVENTION

The following examples illustrate the present invention in further detail. They are, however, by no means limitative of the scope of the invention.

EXAMPLE 1

A 2-liter separable flask provided with a thermocouple for measuring the temperature of the reaction system and a stirrer was charged with 1,4-diisopropylbenzene (44 g), monochlorobenzene (120 g) and an aqueous solution of sodium hypochlorite (1,200 g, 0.9 mol/kg), and the mixture was cooled on an ice bath with stirring at 240 rpm. Then, from a dropping funnel, concentrated hydrochloric acid (80 g, 35% by weight) was added slowly over 3 minutes and the resulting mixture was then stirred further for 60 minutes. Until this timepoint, the procedure was conducted in a closed system, and the gas generated during the reaction was led to an alkali trap (25% aqueous solution of NaOH) and the amount of chlorine gas possibly generated was measured by titration, resulting in no detection. After completion of the reaction, the reaction mixture was allowed to stand and separate into an organic layer and an aqueous layer. Concentrated hydrochloric acid (30 g) was added to the organic layer and the resulting mixture was stirred vigorously for about 5 minutes to thereby deactivate the hypochlorous acid finely dispersed in the organic layer. The organic layer was separated and dried over anhydrous magnesium sulfate to give the reaction product in the form of a monochlorobenzene solution. The yield of 1,4-bis(1-chloro-1-methylethyl)benzene in the reaction product was determined by $^1$H NMR with DMSO (dimethyl sulfoxide) as an internal standard (yield 80.0%).

The $^1$H NMR spectrum obtained showed the following absorptions ascribable to the protons of the starting material [1,4-diisopropylbenzene], the monochlorinated compound [p-(1-chloro-1-methylethyl)isopropylbenzene, reaction intermediate] and the desired product [1,4-bis(1-chloro-1-methylethyl)benzene], respectively.

The measuring apparatus used was Varian model Gemini-300 (300 MHz) and the measurement solvent used was deuteriochloroform.

1,4-Diisopropylbenzene: d=7.16 (s, 4H, aromatic ring), d=2.90 (m, 2H, methines of isopropyl groups), d=1.25 (d, 12H, methyl groups)

p-(1-Chloro-1-methylethyl)isopropylbenzene: d=7.50 (d, 2H, aromatic ring), d=7.20 (d, 2H, aromatic ring), d=3.10 (m, 1H, methine of isopropyl group), d=2.00 (s, 6H, methyl groups each at position β to chloro group), d=1.25 (d, 6H, methyl groups of isopropyl groups)

1,4-Bis(1-chloro-1-methylethyl)benzene: d=7.56 (s, 4H, aromatic ring), d=2.00 (s, 12H, methyl groups).

EXAMPLE 2

A 2-liter separable flask provided with a thermocouple for measuring the temperature of the reaction system and a stirrer was charged with 1,4-diisopropylbenzene (44 g), monochlorobenzene (120 g) and an aqueous solution of sodium hypochlorite (1,200 g, 0.9 mol/kg), and the mixture was cooled on an ice bath with stirring at 240 rpm. Then, from a dropping funnel, concentrated hydrochloric acid (80 g, 35% by weight) was added slowly over 3 minutes and the resulting mixture was stirred further for 60 minutes. Until this timepoint, the procedure was conducted in a closed system, and the gas generated during the reaction was led to an alkali trap (25% aqueous solution of NaOH) and the amount of chlorine gas possibly generated was measured by titration, resulting in no detection. After 60 minutes, the hypochlorous acid concentration in the reaction system was measured, and an aqueous solution of sodium hydroxide (10% by weight) was added in an amount of 2 moles per mole of the remaining hypochlorous acid. After about 5 minutes of stirring, an aqueous solution of sodium sulfite (10%) was added in an amount of 2 moles per mole of the remaining hypochlorous acid, and the whole was stirred for about 5 minutes to deactive the hypochlorous acid. After this deactivation procedure, 100 ml of hexane was further added for effecting extraction. The organic layer was separated, and this mixed solution was washed with three portions of water and dried over magnesium sulfate to give the reaction product in the form of a monochlorobenzene solution. The yield of 1,4-bis(1-chloro-1-methylethyl)benzene in the product was determined by $^1$H NMR with DMSO (dimethyl sulfoxide) as an internal standard (yield 75.0%).

EXAMPLE 3

A 500-mL separable flask provided with a thermocouple for measuring the temperature of the reaction system and a stirrer was charged with 1,4-diisopropylbenzene (7.31 g), and monochlorobenzene (18.75 ml), and the reaction system was set at 0° C. using an ice bath. In another vessel, hypochlorous acid was prepared by adding hydrochloric acid to an aqueous solution of sodium hypochlorite to pH 5 and this was added to the reaction system. The addition amount of hypochlorous acid was 2.8 equivalents of aqueous solution thereof per terminus of the starting material (378 g, 0.667 mol/kg). The total amount was added over 30 minutes by using a dropping funnel. Thereafter, the whole was stirred further for 30 minutes (500 rpm). After completion of the reaction, the reaction mixture was allowed to stand and separate into an organic layer and an aqueous layer. The hypochlorous acid finely dispersed in the organic layer was deactivated by adding concentrated hydrochloric acid (10 g) to the organic layer, followed by about 5 minutes of vigorous stirring. The organic layer was separated and dried over anhydrous magnesium sulfate to give the reaction product in the form of a monochlorobenzene solution. The yield of 1,4-bis(1-chloro-1-methylethyl)benzene in the product was determined by $^1$H NMR with DMSO (dimethyl sulfoxide) as an internal standard (yield 60.0%).

EXAMPLE 4

A 2-liter separable flask provided with a thermocouple for measuring the temperature of the reaction system and a stirrer was charged with 1,4-diisopropylbenzene (44 g) and an aqueous solution of sodium hypochlorite (1,200 g, 0.9 mol/kg), and the mixture was cooled on an ice bath with stirring at 240 rpm. Then, from a dropping funnel, concentrated hydrochloric acid (80 g, 35% by weight) was added slowly over 3 minutes and the resulting mixture was stirred further for 60 minutes. Until this timepoint, the procedure was conducted in a closed system, and the gas generated during the reaction was led to an alkali trap (25% aqueous solution of NaOH) and the amount of chlorine gas possibly generated was measured by titration, resulting in no detection. After completion of the reaction, the reaction mixture was allowed to stand and separate into an organic layer and an aqueous layer. The hypochlorous acid finely dispersed in the organic layer was deactivated by adding concentrated hydrochloric acid (30 g) to the organic layer, followed by about 5 minutes of vigorous stirring. The organic layer was separated and dried over anhydrous magnesium sulfate to give the reaction product in the form of a monochlorobenzene solution. The yield of 1,4-bis(1-chloro-1-methylethyl)benzene in the product was determined by $^1$H NMR with DMSO (dimethyl sulfoxide) as an internal standard (yield 55.0%).

EXAMPLE 5

The reaction was carried out in the same manner as in Example 1 except that trifluoromethylbenzene was used in lieu of monochlorobenzene (yield 56.0 mole %).

Comparative Example 1

In the following, a process in which hypochlorous acid is prepared in advance in another vessel and this is added to the starting material to thereby initiate the reaction and in which the organic layer after termination of the reaction is not contacted with an acid is described in detail. The yield in said process is also given below.

A 500-mL separable flask provided with a thermocouple for measuring the temperature of the reaction system and a stirrer was charged with 1,4-diisopropylbenzene (7.31 g), and monochlorobenzene (18.75 ml), and the reaction system was set at 0° C. by using an ice bath. In another vessel, hypochlorous acid was prepared by adding hydrochloric acid to an aqueous solution of sodium hypochlorite to pH 5 and this was added to the reaction system. The addition amount of hypochlorous acid was 2.8 equivalents of aqueous solution thereof per terminus of the starting material (378 g, 0.667 mol/kg). The total amount was added over 30 minutes by using a dropping funnel. Thereafter, the whole was stirred further for 30 minutes (500 rpm). After completion of the reaction, the hypochlorous acid concentration in the reaction system was measured, and an aqueous solution of sodium hydroxide (10% by weight) was added in an amount of 2 moles per mole of the remaining hypochlorous acid and stirred for about 5 minutes. An aqueous solution of sodium sulfite (10%) was added in an amount of 2 moles per mole of the remaining hypochlorous acid, and the whole was stirred for about 5 minutes to deactive the hypochlorous acid. After this deactivation procedure, 100 ml of hexane was further added for effecting extraction. The organic layer was separated, and this mixed solution was washed with three portions of water and dried over magnesium sulfate to give the reaction product in the form of a monochlorobenzene solution. The yield of 1,4-bis(1-chloro-1-methylethyl) benzene in the product was determined by $^1$H NMR with DMSO (dimethyl sulfoxide) as an internal standard (yield 45.0%).

EXAMPLE 6

A glass-lined vessel having an inside diameter of 1.3 m was charged with 1.5 m$^3$ of a hexane solution containing 1,4-dicumyl chloride and monochlorobenzene, and crystallization under cooling was effected in the presence of 50 kg of 35% by weight aqueous hydrochloric acid with stirring. After completion of the crystallization procedure, the surface of the lining was observed. No pinhole was found.

Comparative Example 2

A glass-lined vessel having an inside diameter of 2 m was charged with 2.9 m$^3$ of a hexane solution containing 1,4-dicumyl chloride, and crystallization under cooling was effected with stirring. After completion of the crystallization procedure, the surface of the lining was observed. At least 50 pinholes were found.

According to the present invention, the tertiary carbon atom or atoms of the hydrocarbon compound of general formula (1) can be selectively chlorinated with high efficiency. Furthermore, the compound of general formula (2) with chlorine introduced on the tertiary carbon atom or atoms thereof is very unstable but can be obtained as a product stable in quality. In the conventional processes in which hypochlorous acid is used as the chlorinating reagent, generation of dangerous chlorine gas is involved in the step of preparing hypochlorous acid and, moreover, the hypochlorous acid after preparation is very unstable and it is difficult to prepare and store hypochlorous acid always with a constant concentration. Therefore, for obtaining the product always constant in quality by maintaining constant the equivalent relationship between hypochlorous acid and the compound of general formula (1), it is necessary to measure each time the chlorine concentration of hypochlorous acid and adjust the amount thereof to be fed so that the prior art processes are very difficult to practice from the industrial application viewpoint. On the contrary, according to the present invention, it is possible to maintain always constant the equivalent relationship between the starting material (1) and hypochlorous acid without measuring the chlorine concentration of hypochlorous acid, and the product can be obtained always in a constant composition in a simple process with good reproducibility. Furthermore, quality deterioration resulting from reaction termination is prevented and the product can be obtained always with a constant quality. From the industrial application viewpoint, it is necessary to use a glass-lined vessel, and the greatest problem in that case, namely the necessity of taking measures against electrostatic charging, can be solved by adding hydrochloric acid and safety can be assured thereby.

Therefore, the present invention can be said to provide a practical process for producing a chlorinated tertiary carbon-containing hydrocarbon of general formula (2).

What is claimed is:

1. A process for producing (D) a chlorinated hydrocarbon compound of the general formula (2):

$$C_nR^1{}_mH_k(CR^2R^3Cl)_j \qquad (2)$$

[wherein n is an integer of 1 to 12, m and k each independently is an integer of 0 to 25, j is an integer of 1 to 10; R$^1$ represents an atom selected from the group consisting of chlorine, bromine, iodine, oxygen, nitrogen, sulfur and phosphorus and, when m is 2 or more, the two or more R$^1$ groups may be the same or different, the group C$_n$R$^1{}_m$H$_k$ having a valence of j does not contain any tertiary carbon-hydrogen bond; and R$^2$ and R$^3$ each independently represents a saturated aliphatic hydrocarbon group containing 1 to 5 carbon atoms or a group derived therefrom by substitution of a halogen atom or atoms for some hydrogen atom or atoms thereof and not containing a tertiary carbon-hydrogen bond], which comprises adding (C) a protic acid to a mixture of (A) a compound of the general formula (1):

$$C_nR^1{}_mH_k(CHR^2R^3)_j \qquad (1)$$

and (B) an aqueous solution of a metal hypochlorite.

2. A process for producing a chlorinated hydrocarbon compound which comprises synthesizing (D) a compound of the general formula (2):

$$C_nR^1{}_mH_k(CR^2R^3Cl)_j \qquad (2)$$

by using (A) a compound of the general formula (1):

$$C_nR^1{}_mH_k(CHR^2R^3)_j \qquad (1)$$

(B) an aqueous solution of a metal hypochlorite and
(C) a protic acid,
and thereafter adding
(E) a protic acid to the organic layer.

3. The process according to claim 1 wherein (F) an organic solvent is used when synthesizing
(D) the compound of the general formula (2):

$$C_nR^1{}_mH_k(CR^2R^3Cl)_j \qquad (2)$$

[wherein m, n, k, j, R$^1$, R$^2$ and R$^3$ are as defined above], by using
(A) the compound of the general formula (1):

$$C_nR^1{}_mH_k(CHR^2R^3)_j \qquad (1)$$

(B) the aqueous solution of a metal hypochlorite and
(C) the protic acid.

4. The process according to claim 1, wherein (A) the compound of general formula (1) is an isopropyl-substituted group-containing aromatic hydrocarbon, the metal hypochlorite (B) is selected from the group consisting of potassium hypochloride, sodium hypochlorite, calcium hypochlorite, barium hypochlorite, cuprous hypochlorite and cupric hypochlorite, and the protic acid (C) is hydrogen chloride.

5. The process according to claim 1 wherein at least one member of the group consisting of toluene, benzene, monochlorobenzene, dichlorobenzene, trichlorobenzene, ethyl chloride, ethylene dichloride, carbon tetrachloride, chloroform, methylene chloride, butyl chloride, propyl chloride, 1-trichloro-2-trifluoroethane and trifluoromethylbenzene is used as a reaction solvent.

6. The process according to claim 1, wherein the protic acid (C) is selected from the group consisting of hydrochloric acid, sulfuric acid and acetic acid.

7. The process according to claim 1 wherein the product of hydrolysis of the compound of general formula (2) occurring in the organic layer after the reaction is brought into contact with hydrochloric acid to thereby produce the compound of general formula (2).

8. The process according to claim 1 wherein, after the reaction, the organic layer and aqueous layer are separated from each other, the aqueous layer is made alkaline, and followed by adding sodium sulfite to said aqueous layer.

9. The process according to claim 2 wherein (F) an organic solvent is used when synthesizing (D) the compound of the general formula (2):

$$C_nR^1{}_mH_k(CR^2R^3Cl)_j \qquad (2)$$

wherein m n k, j $R^1$, $R^2$ and $R^3$ are as defined above, by using (A) the compound of the general formula (1):

$$C_nR^1{}_mH_k(CHR^2R^3)_j \qquad (1)$$

wherein m, n, k, j, $R^1$, $R^2$ and $R^3$ are as defined above, (B) the aqueous solution of a metal hypochlorite and (C) the protic acid.

10. The process according to claim 2 wherein (A) the compound of general formula (1) is an isopropyl-substituted group-containing aromatic hydrocarbon, the metal hypochlorite (B) is selected from the group consisting of potassium hypochloride, sodium hypochlorite, calcium hypochlorite, barium hypochlorite, cuprous hypochloride and cupric hypochlorite, and the protic acid (C) is hydrogen chloride.

11. The process according to claim 3 wherein (A) the compound of general formula (1)is an isopropyl-substituted group-containing aromatic hydrocarbon, the metal hypochlorite (B) is selected from the group consisting of potassium hypochloride, sodium hypochlorite, calcium hypochlorite, barium hypochlorite, cuprous hypochloride and cupric hypochlorite, and the protic acid (C) is hydrogen chloride.

12. The process according to claim 2 wherein at least one member of the group consisting of toluene, benzene, monochlorobenzene, dichlorobenzene, trichlorobenzene, ethyl chloride, ethylene dichloride, carbon tetrachloride, chloroform, methylene chloride, butyl chloride, propyl chloride, 1-trichloro-2-trifluoroethane and trifluoromethylbenzene is used as a reaction solvent.

13. The process according to claim 3 wherein at least one member of the group consisting of toluene, benzene, monochlorobenzene, dichlorobenzene, trichlorobenzene, ethyl chloride, ethylene dichloride, carbon tetrachloride, chloroform, methylene chloride, butyl chloride, propyl chloride, 1-trichloro-2-trifluoroethane and trifluoromethylbenzene is used as a reaction solvent.

14. The process according to claim 4 wherein at least one member of the group consisting of toluene, benzene, monochlorobenzene, dichlorobenzene, trichlorobenzene, ethyl chloride, ethylene dichloride, carbon tetrachloride, chloroform, methylene chloride, butyl chloride, proply chloride, 1-trichloro-2-trifluoroethane and trifluoromethylbenzene is used as a reaction solvent.

15. The process according to claim 2 wherein the protic acid (C) is selected from the group consisting of hydrochloric acid, sulfuric acid and acetic acid.

16. The process according to claim 3 wherein the protic acid (C) is selected from the group consisting of hydrochloric acid, sulfuric acid and acetic acid.

17. The process according to claim 3 wherein the product of hydrolysis of the compound of general formula (2) occurring in the organic layer after the reaction is brought into contract with hydrochloric acid to thereby produce the compound of general formula (2).

18. The process according to claim 4 wherein the product of hydrolysis of the compound of general formula (2) occurring in the organic layer after the reaction is brought into contact with hydrochloric acid to thereby produce the compound of general formula (2).

19. The process according to claim 5 wherein the product of hydrolysis of the compound of general formula (2) occurring in the organic layer after the reaction is brought into contact with hydrochloric acid to thereby produce the compound of general formula (2).

* * * * *